(12) United States Patent
Scannell

(10) Patent No.: US 10,251,397 B2
(45) Date of Patent: Apr. 9, 2019

(54) USE OF BENTONITE FOR IMPROVING PLANT GROWTH-RELATED TRAITS

(71) Applicant: Christopher Scannell, Marblehead, MA (US)

(72) Inventor: Christopher Scannell, Marblehead, MA (US)

(*) Notice: Subject to any disclaimer, the term of this patent is extended or adjusted under 35 U.S.C. 154(b) by 152 days.

(21) Appl. No.: 15/441,523

(22) Filed: Feb. 24, 2017

(65) Prior Publication Data
US 2017/0156337 A1 Jun. 8, 2017

Related U.S. Application Data

(63) Continuation of application No. PCT/US2016/018370, filed on Feb. 18, 2016.

(60) Provisional application No. 62/118,198, filed on Feb. 19, 2015.

(51) Int. Cl.
| | |
|---|---|
| *A01N 59/06* | (2006.01) |
| *A01G 22/00* | (2018.01) |
| *A01G 13/00* | (2006.01) |
| *A01C 21/00* | (2006.01) |
| *C05D 9/00* | (2006.01) |

(52) U.S. Cl.
CPC ............ *A01N 59/06* (2013.01); *A01C 21/005* (2013.01); *A01G 13/00* (2013.01); *A01G 22/00* (2018.02); *C05D 9/00* (2013.01)

(58) Field of Classification Search
CPC ...... A01N 59/06; A01C 21/005; C09K 17/02; C09K 17/06; C09K 17/04; C09K 17/46; C09K 17/08; A01G 22/00; A01G 13/00; C05D 9/00
See application file for complete search history.

(56) References Cited

U.S. PATENT DOCUMENTS

| | | | | |
|---|---|---|---|---|
| 3,336,129 A | * | 8/1967 | Herrett | A01C 1/046 504/360 |
| 3,973,355 A | * | 8/1976 | McKenzie | A01G 24/44 47/59 R |
| 4,034,507 A | * | 7/1977 | Dedolph | A01G 9/02 47/64 |
| 4,069,034 A | * | 1/1978 | Hoover | C05B 7/00 23/300 |

(Continued)

FOREIGN PATENT DOCUMENTS

WO WO 2014070606 A1 * 5/2014 ............ A01N 43/16

OTHER PUBLICATIONS

British Geological Survey 1993, Technical Report WG/93/20 Mineralogy and Petrology Series, Industrial Minerals Laboratory Manual Bentonite; SDJ Inglethorpe, DJ Morgan, DE Highley and AJ Bloodworth.

(Continued)

*Primary Examiner* — Joshua D Huson
(74) *Attorney, Agent, or Firm* — McCarter & English, LLP; Marcie B. Clarke

(57) ABSTRACT

The present invention relates to a slurry comprising water, bentonite, and a compound selected from fertilizer, a plant growth regulator, a fungicide and an insecticide. The present invention also relates to an agricultural product comprising a slurry comprising water and bentonite, and a plant propagative material. Methods of using the bentonite to enhance a growth-related trait, such as drought tolerance, in a plant are also described.

30 Claims, 5 Drawing Sheets

(56) References Cited

U.S. PATENT DOCUMENTS

| | | | | |
|---|---|---|---|---|
| 4,074,997 | A * | 2/1978 | Cohen | A01G 24/00 71/24 |
| 4,114,316 | A * | 9/1978 | Cohen | A01G 24/00 47/64 |
| 4,238,374 | A * | 12/1980 | Durham | A01G 5/06 47/41.1 |
| 4,241,537 | A * | 12/1980 | Wood | C08G 18/4837 47/77 |
| 4,278,625 | A * | 7/1981 | Dedolph | A01C 11/02 264/39 |
| 5,218,783 | A * | 6/1993 | Langezaal | A01G 24/00 47/64 |
| 5,759,225 | A * | 6/1998 | Tanoshima | C05D 9/00 71/24 |
| 7,117,634 | B2 * | 10/2006 | Pelton | A01G 24/28 47/77 |
| 7,866,090 | B2 * | 1/2011 | Langezaal | A01G 24/00 47/58.1 R |
| 8,544,207 | B2 * | 10/2013 | King | A01G 31/02 47/59 S |
| 8,637,091 | B2 * | 1/2014 | Pluta | A01N 25/08 424/683 |
| 2003/0159349 | A1 * | 8/2003 | Glenn | A01N 59/00 47/58.1 SC |
| 2004/0045217 | A1 * | 3/2004 | Chiddick | A01G 24/00 47/59 S |
| 2004/0049980 | A1 * | 3/2004 | Principe | A01G 24/30 47/64 |
| 2004/0235168 | A1 * | 11/2004 | Langezaal | A01G 24/00 435/404 |
| 2006/0117655 | A1 * | 6/2006 | Bodycomb | A01G 24/00 47/59 S |
| 2006/0252649 | A1 * | 11/2006 | Pluta | A01N 25/08 504/367 |
| 2008/0250711 | A1 * | 10/2008 | Everhardus Lucas Langezaal | A01G 24/00 47/77 |
| 2009/0076190 | A1 * | 3/2009 | Park | A01G 24/00 523/123 |
| 2010/0267554 | A1 | 10/2010 | Madsen et al. | |
| 2011/0094967 | A1 * | 4/2011 | Glienke | C05D 9/00 210/660 |
| 2011/0263431 | A1 * | 10/2011 | Corsi | C07D 401/06 504/242 |
| 2012/0220454 | A1 | 8/2012 | Chen et al. | |
| 2012/0278956 | A1 * | 11/2012 | Hartman | A01G 24/00 800/323 |
| 2013/0143737 | A1 * | 6/2013 | Varadachari | C05B 13/06 504/101 |
| 2013/0145805 | A1 * | 6/2013 | Olson | C05D 9/00 71/6 |
| 2015/0225305 | A1 * | 8/2015 | Donze | C05G 3/04 71/23 |
| 2015/0282482 | A1 * | 10/2015 | Mukumoto | A01N 43/12 504/100 |
| 2016/0002118 | A1 * | 1/2016 | Varadachari | C05B 13/06 71/29 |
| 2017/0164562 | A1 * | 6/2017 | Nonomura | A01G 22/00 |

OTHER PUBLICATIONS

Elements An International Magazine of Mineralogy, Geochemistry, and Petrology; Bentonites Versatile Clays; Derek C. Bain; Apr. 2009; vol. 5, No. 2; ISSN 1811-5209.

International Search Report for PCT/US2016/018370, dated Apr. 21, 2016.

* cited by examiner

Control        Green bentonite + IAA        Bentonite + fertilizer

White bentonite     Green bentonite     White bentonite + IAA

Control     Green bentonite + IAA    Bentonite + fertilizer

White bentonite     Green bentonite     White bentonite + IAA

USE OF BENTONITE FOR IMPROVING PLANT GROWTH-RELATED TRAITS

RELATED APPLICATIONS

This application is a continuation under 35 U.S.C. § 111(a) of International Application No. PCT/US2016/018370, filed Feb. 18, 2016 which, in turn, claims priority to U.S. Provisional Patent Application No. 62/118,198 filed on Feb. 19, 2015, the contents of each of which are expressly incorporated herein by reference in their entirety.

FIELD OF THE INVENTION

The present invention relates to the use of bentonite for enhancing a growth-related trait in a plant.

BACKGROUND OF THE INVENTION

Stand establishment refers to the production of a uniform population of healthy seedlings of agricultural crops. The stand of an agricultural crop may be established through direct seeding into the field, or by the planting of transplants. Successful crop production and optimum yields can be accomplished only when maximum stand establishment is achieved. (Grassbaugh et al., 1998, Sci. agric., Piracicaba, 55 (Edicao Especial): 116-120). Stand reduction generally results in reduced yields and variable crop quality. Several factors contribute to stand establishment in the production of agricultural crops. Environmental factors such as drought, temperature stress and unfavorably soil conditions, as well as pathogens and insects that attack seeds and seedlings can all contribute to reduced stands (Orzolek, 1991, HortTechnology 1: 78-81). For direct-seeded crops, uneven germination results in seedlings of various sizes and gaps in the planting row, which can ultimately result in reduced yields. For transplanted crops, poor transplant survival rates or slow initiation of plant growth after transplanting can result in reduced plant populations and uneven stands. In addition, cultural practices such as herbicide and insecticide applications after transplanting or seed emergence may be less effective in fields having nonuniform growth (Bennett et al., 1992, HortTechnology 2(3): 345-349). Plants of different sizes within a field population may also cause problems in timing sidedress applications of fertilizers (Ford, 1987, Crops and Soils Magazine, p. 12-13, April/May, 1987). Thus, measures to lessen the impact of environmental stresses and various pests are vital in the successful establishment of agricultural crop stands. The ability of plants to survive stresses imposed by environmental conditions and pest infestations greatly depends on the initial vigor of the stand at establishment.

Dry seed coating is one method that has been developed to improve establishment of direct-seeded crops. For example, US 2012/0220454 describes seed coating compositions that may comprise more than one layer, for example, a first layer comprising a film forming layer, a second layer comprising a binding agent, and a third layer comprising a wetting agent. See US 2012/0220454, paragraph [0019]. In addition US 2012/0220454 teaches that the seed coating compositions can flow better through a seeding mechanism, because their surface is smoother than that of non-coated seed. See US 2012/0220454, paragraph [0021].

US 2010/0267554 describes coating seeds with a wetting agent such as copolymers, block copolymers, alcohol ethoxylates, nonylphenol ethoxylates, ethylene oxide/propylene oxide block copolymers, and alkylpolyglycosides for planting in hydrophobic soils. See US 2010/0267554, paragraphs [0022] and [0023].

Despite the potential advantages of seed coating technologies, a need still exists for improving stand establishment for direct-seeded and transplanted food crops and ornamental plants.

SUMMARY OF THE INVENTION

In one aspect, the invention provides a composition comprising a slurry comprising at least about 50% w/w of water and from about 1% to about 50% w/w of bentonite; and a plant propagative material. In one embodiment, the slurry further comprises a compound selected from the group consisting of a fertilizer, a plant growth regulator, a fungicide, an insecticide, an amino acid, a peptide, a protein, and a nucleic acid. In one embodiment, the plant growth regulator is selected from the group consisting of auxins, giberellins, cytokinins, ethylene-related compounds, abscisic acid, brassinosteroids, jasmonates, polyamines, karrikins, and any combination thereof. In another embodiment, the slurry further comprises a fertilizer comprising nitrogen, and the nitrogen is at a concentration from about 10 ppm (w/w) of the slurry to about 2000 ppm (w/w) of the slurry. In another embodiment, the slurry further comprises a plant growth regulator at a concentration from about 10 ppm to about 1000 ppm. In one embodiment, the plant propagative material is a seed.

In another aspect, the invention provides a composition comprising a supersaturated bentonite slurry comprising bentonite and water; and a plant propagative material.

In another aspect, the invention provides a supersaturated bentonite slurry comprising bentonite, water, and a compound selected from the group consisting of a fertilizer, a plant growth regulator, a fungicide and an insecticide.

In another aspect, the invention provides a slurry comprising water, from about 10% (w/w) to about 50% (w/w) of bentonite, and a compound selected from the group consisting of a fertilizer, a plant growth regulator, a fungicide and an insecticide.

In one embodiment, the plant growth regulator is selected from the group consisting of auxins, giberellins, cytokinins, ethylene-related compounds, abscisic acid, brassinosteroids, jasmonates, polyamines, karrikins, and any combination thereof. In another embodiment, the slurry comprises a fertilizer comprising nitrogen, and the nitrogen is at a concentration from about 10 ppm (w/w) of the slurry to about 2000 ppm (w/w) of the slurry. In another embodiment, the slurry comprises from about 10 ppm to about 1000 ppm of the plant growth regulator.

In another aspect, the invention provides a method of enhancing a growth-related trait in a plant propagative material relative to a control plant propagative material, comprising a) applying a slurry comprising bentonite and water to a plant growth medium; and b) introducing the plant propagative material into the plant growth medium containing the slurry, wherein the growth-related trait of the plant propagative material is enhanced relative to a control plant propagative material that is not treated with the slurry.

In one embodiment, the growth-related trait is selected from the group consisting of total seed germination, rate of seed germination, plant biomass, insect tolerance, herbivore tolerance, and drought tolerance. In another embodiment, the growth-related trait is enhanced under drought conditions. In another embodiment, the slurry further comprises at least one compound selected from the group consisting of a fertilizer, a plant growth regulator, a fungicide, an insecticide, an amino acid, a peptide, a protein, and a nucleic acid. In another embodiment, the plant growth regulator is selected from the group consisting of auxins, giberellins, cytokinins, ethylene-related compounds, abscisic acid, brassinosteroids, jasmonates, polyamines, karrikins, and any combination thereof.

In one embodiment, the bentonite is selected from the group consisting of sodium bentonite and calcium bentonite. In one embodiment, the plant propagative material is a seed.

In another embodiment, the slurry is a supersaturated bentonite slurry. In another embodiment, the slurry is applied to a discrete area of the plant growth medium.

In another aspect, the invention provides a method of enhancing a growth-related trait in a plant propagative material relative to a control plant propagative material, comprising a) contacting a slurry comprising bentonite and water with a plant propagative material; and b) introducing the plant propagative material contacted with the slurry into a plant growth medium; wherein the growth-related trait of the plant propagative material is enhanced relative to a control plant propagative material that is not treated with the slurry.

In one embodiment, the growth-related trait is selected from the group consisting of total seed germination, rate of seed germination, plant biomass, insect tolerance, herbivore tolerance, and drought tolerance. In another embodiment, the growth-related trait is enhanced under drought conditions.

In one embodiment, the slurry further comprises at least one compound selected from the group consisting of a fertilizer, a plant growth regulator, an insecticide, a fungicide, an amino acid, a peptide, a protein, and a nucleic acid. In one embodiment, the plant growth regulator is selected from the group consisting of auxins, giberellins, cytokinins, ethylene-related compounds, abscisic acid, brassinosteroids, jasmonates, polyamines, karrikins, and any combination thereof.

In one embodiment, the bentonite is selected from the group consisting of calcium bentonite and sodium bentonite. In another embodiment, the plant propagative material is a seed. In one embodiment, the slurry is a supersaturated bentonite slurry. In one embodiment, the plant growth regulator is selected from the group consisting of auxins, giberellins, cytokinins, ethylene-related compounds, abscisic acid, brassinosteroids, jasmonates, polyamines, karrikins, and any combination thereof.

In one embodiment, the slurry further comprises a compound selected from the group consisting of an amino acid, a peptide, a protein, and a nucleic acid.

In another aspect, the invention provides a method of enhancing a growth-related trait in a plant propagative material relative to a control plant propagative material, comprising a) applying bentonite to a discrete area of a plant growth medium; and b) introducing the plant propagative material into the discrete area of the plant growth medium containing the bentonite, wherein the growth-related trait of the plant propagative material is enhanced relative to a control plant propagative material that is not treated with the bentonite.

In one embodiment, the bentonite is applied at a rate of less than about 1000 kg/acre. In another embodiment, the bentonite is applied to less than 50% of the surface of the plant growth medium.

DETAILED DESCRIPTION OF THE INVENTION

Figure 1:
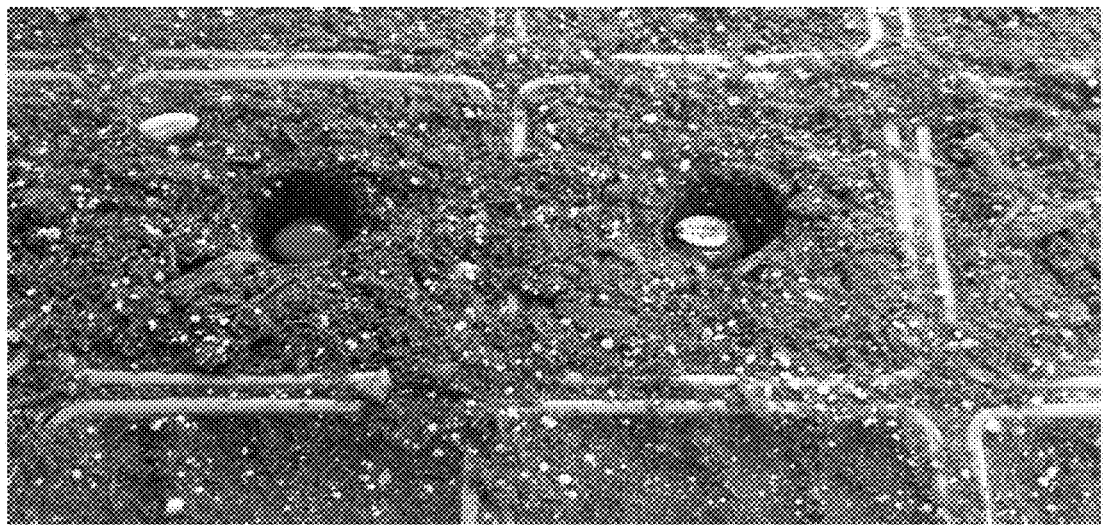
FIG. 1 shows slurry comprising bentonite and water placed in the planting holes in potting soil before planting of sunflower seeds.
Figure 2:
FIG. 2 shows sunflower seedlings 12 days after planting. Sunflower seeds were untreated (control) or treated with a green bentonite and 200 ppm IAA slurry (green bentonite+IAA), or a bentonite and MIRACLE-GRO fertilizer slurry (bentonite+fertilizer) at the time of planting. In the bentonite+fertilizer treatment group, the seeds in the top three pots were treated with white bentonite and fertilizer and the plants in the bottom three pots were treated with green bentonite and fertilizer.
Figure 3:
FIG. 3 shows sunflower seedlings 12 days after planting. Sunflower seeds were treated with a white bentonite slurry, a green bentonite slurry, or a white bentonite and 200 ppm IAA slurry (white bentonite+IAA) at the time of planting.
Figure 4:
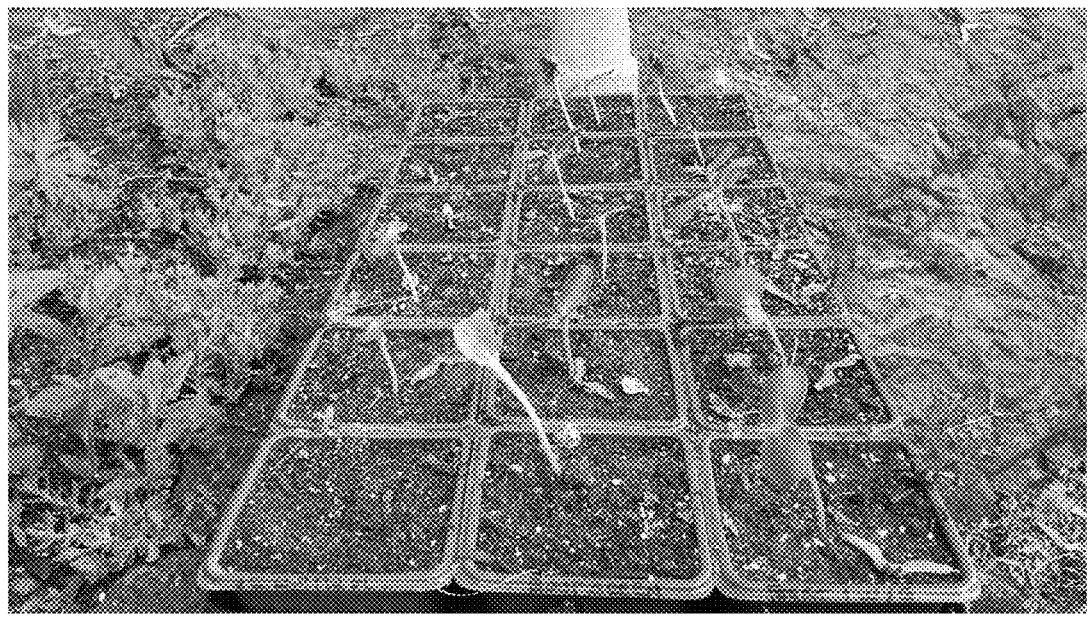
FIG. 4 shows sunflower seedlings 18 days after planting. Sunflower seeds were untreated (control) or treated with a green bentonite and 200 ppm IAA slurry (green bentonite+IAA) or a bentonite and MIRACLE-GRO fertilizer slurry (bentonite+fertilizer). In the bentonite+fertilizer treatment group, the seeds in the top three pots were treated with white bentonite and fertilizer and the plants in the bottom three pots were treated with green bentonite and fertilizer.
Figure 5:
FIG. 5 shows sunflower seedlings 18 days after planting. Sunflower seeds were treated with a white bentonite slurry, a green bentonite slurry, or a white bentonite and 200 ppm IAA slurry (white bentonite+IAA) at the time of planting.

The present invention relates to the use of a bentonite slurry for enhancing a growth-related trait in a plant. Unlike previously used seed coatings, the water-based slurry comprising bentonite of the invention immediately introduces a hydrated microcosm that induces seed germination. For example, the slurry provides a hydrated microenvironment to the seed that keeps the seed shell moist and promotes water absorption into the shell. This in turn allows the shell to swell and eventually crack and initiate germination. Intermittent drought stress is mitigated, as the slurry volume maintains a hydrated environment to promote seed shell swelling and germination. Once the seed shell has swollen and cracked, plant growth regulators and fertilizer in the slurry can enhance germination and rooting activity and expedite emergence of the seedling from the soil and early growth of the developing seedling.

Bentonite is a naturally absorbent clay consisting mostly of montmorillonite, which is part of the smectite group of clays. It is a silicate bilayer that sandwiches a cation (e.g., Na, Ca, or Mg), and is hygroscopic to varying extents. The different types of bentonite are named after the dominant element which they comprise, for example potassium (K), sodium (Na), calcium (Ca), aluminum (Al), or magnesium (Mg). There are two main classes of bentonite used for industrial purposes: sodium bentonite and calcium bentonite. When mixed with water, sodium bentonites exhibit a greater degree of swelling, a greater degree of dispersion, and better plastic and rheological properties than calcium bentonites. See Inglethorpe et al., 1993, Bentonite, Industrial Mineral Laboratory Manual, Technical Report WG/93/20, Mineralogy and Petrology Series, British Geological Survey, pages 1-116. For example, sodium bentonite has the ability to absorb four to five times its own weight in water and can swell five to fifteen times its dry volume at full-unconfined saturation.

The Swell Index or Free Swell test procedure is typically used to determine the swelling characteristics of bentonite. Several methods are well known in the art to determine the swelling characteristics of bentonite, including the Swell Index or Free Swell test. For example, one test method involves placing a 100 gram sample of bentonite in a six-inch diameter cylinder equipped with a porous plate/dial gauge indicator. The apparatus is placed in a pan of water for twenty-four hours, at which time the dial gauge is read for the swell increase. Results of this index test are used to determine the swelling characteristics of the bentonite sample. Because of its colloidal properties, bentonite is often used in drilling mud for oil and gas wells and boreholes for geotechnical and environmental investigations. Calcium bentonite is an adsorbent of ions in solution. Potassium bentonite is a potassium-rich illitic clay formed from alteration of volcanic ash. White bentonite is derived from weathered volcanic ash and is predominately calcium bentonite which has a high cation exchange capacity and low crystalline silica (cristobalite). Green bentonite may be a sodium bentonite or may contain other cations. The green color of green bentonite results from $Fe^{++}$ ions contained in the bentonite. The exchangeable cations in bentonite are easily replaceable. For example, ion exchange from $Ca^+$ to $Na^+$ requires only mixing, and calcium bentonite may be converted to sodium bentonite by adding sodium bicarbonate to improve swelling properties. In natural bentonite deposits, $Na^+$ is readily replaced by $Ca^+$ and $Mg^+$ under leaching conditions. See Inglethorpe et al., cited above. Table 1 below provides the chemical composition of various calcium bentonites and sodium bentonites.

TABLE 1

X-ray diffraction analysis of bentonite samples

| Sample | Na/Ca | Montmorillonite | Mica | Gypsum | Opal | Quartz | Feldspar | Calcite |
|---|---|---|---|---|---|---|---|---|
| 1 | Ca | 76% | 0% | 10% | 6% | 4% | 4% | 0% |
| 2 | Na | 73% | 0% | 0% | 3% | 9% | 15% | 0% |
| 3 | Ca | 83% | 0% | 5% | 2% | 9% | 2% | 0% |
| 4 | Ca | 82% | 0% | 6% | 2% | 9% | 2% | 0% |
| 5 | Na | 82% | 0% | 0% | 0.7% | 15% | 3% | 0% |
| 6 | Ca | 81% | 0% | 0% | 0% | 14% | 5% | 0% |
| 7 | Na | 78% | 0% | 7% | 0% | 14% | 1% | 0% |

Table 2 below shows the Swell Index and specific gravity of various bentonites in which 3% sodium bicarbonate has been added.

TABLE 2

Swell Index and specific gravity of various bentonites treated with sodium bicarbonate

| | Sample | | |
|---|---|---|---|
| | 1 | 2 | 3 |
| Swell Index, ml/2 g | 19 | 24 | 20 |
| Specific Gravity | 2.703 | 2.701 | 2.678 |
| % $Na_2CO_3$ | 3% | 3% | 3% |

As described in Example 1 below, Applicants have discovered that when a wetted bentonite slurry is combined with a seed in a planting hole, the hydrated microenvironment increases germination rate and total germination, and increases seedling growth under drought stress conditions. More robust plant development (e.g., root, stem and leaf development) and increased tolerance to herbivores (snails) was also observed for the bentonite treated seeds relative to control seeds that were not treated with bentonite. These improvements in germination and plant growth were observed in seeds treated with bentonite alone, or bentonite in combination with fertilizer (e.g., nitrogen based fertilizer or nitrogen, phosphorus and potassium based fertilizers, such as MIRACLE-GRO, or organic fertilizers), the plant growth regulator indole-3-acetic acid (IAA), or the combination of fertilizers and plant growth regulators. Thus, Applicants have demonstrated that treatment of a plant with a water-based bentonite slurry enhances plant growth-related traits. A water-based bentonite slurry would also allow for flowability from an automatic hopper and dispenser to increase the planting scale.

In certain embodiments, the present invention relates to an agricultural product comprising: a) a slurry comprising bentonite and water; and b) a plant propagative material. In one embodiment, the plant propagative material is at least partially in contact with the slurry. For example, the plant propagative material can be placed on top of the slurry. Alternatively, the plant propagative material can be placed below the slurry. In another embodiment, the plant propagative material (e.g., a seed) is submerged in the slurry.

The articles "a" and "an" are used herein to refer to one or to more than one (i.e., to at least one) of the grammatical object of the article. By way of example, "an element" means one element or more than one element.

As used herein, the term "slurry" refers to a thin sloppy fluid mixture of a pulverized solid with a liquid (usually water). A slurry behaves, in some ways, like a thick fluid and is capable of flowing under gravity but is also capable of being pumped if not too thick. Slurries of the instant invention may comprise bentonite and water. The water-based bentonite slurries of the invention also allow for flowability from an automatic hopper and dispenser to increase the speed of seed planting and the planting scale. Use of a hopper applied bentonite allows a grower to apply bentonite slurry only in the parts of a field where it is needed, for example in dry areas. Thus the use of a bentonite slurry is consistent with precision (GPS guided) agricultural "best practices." This is in contrast to dry seed coating that uses bentonite on all seeds, including in areas where it may not be needed or desirable, such as flood prone parts of the field. Use of a slurry allows for a discreet application of bentonite consistent with modern "precision farming" best practices by only treating areas that need treatment As used herein the term "plant propagative material" refers to all the generative part of a plant that may be used for the multiplication of the plant. Plant propagative materials include, but are not limited to seeds, roots, tubers, bulbs, rhizomes, leaves, seedlings, transplants, plugs, saplings, and nursery stock of trees and shrubs. In one embodiment, the plant propagative material is a seed.

As used herein, the term "plug" refers to a seedling grown in a small, individual cell of a tray (for example, a tray made from expanded polystyrene or polythene) filled with a plant growth medium. Plugs are typically young plants grown in small, individual cells, for transplanting into soil or other larger containers. Plugs are generally raised under controlled conditions for the first few days or weeks of growth. In some embodiments, plugs are treated with a bentonite slurry before transplanting, for example, by applying the slurry to the growth medium. In some embodiments, plugs are treated with a bentonite slurry after transplanting, for example, by adding the slurry to the planting hole after the plug is deposited in the soil. Treatment of plugs with bentonite slurry would be especially beneficial under drought conditions to improve seedling establishment.

Plants that are particularly useful in the present invention include monocotyledonous and dicotyledonous plants including but not limited to fodder or forage legumes, ornamental plants, food crops, trees, or shrubs selected from *Acer* spp., *Allium* spp., *Amaranthus* spp., *Ananas comosus*, *Apium graveolens*, *Arachis* spp, *Asparagus officinalis*, *Beta vulgaris*, *Brassica* spp. (e.g., *Brassica napus*, *Brassica rapa* ssp. [canola, oilseed rape, turnip rape]), *Camellia sinensis*, *Canna indica*, *Cannabis sativa*, *Capsicum* spp., *Castanea* spp., *Cichorium endivia*, *Citrullus lanatus*, *Citrus* spp., *Cocos* spp., *Coffea* spp., *Coriandrum sativum*, *Corylus* spp., *Crataegus* spp., *Cucurbita* spp., *Cucumis* spp., *Daucus carota*, *Fagus* spp., *Ficus carica*, *Fragaria* spp., *Ginkgo biloba*, *Glycine* spp. (e.g., *Glycine max*, *Soja hispida* or *Soja max*), *Gossypium hirsutum*, *Helianthus* spp. (e.g., *Helianthus annuus*), *Hibiscus* spp., *Hordeum* spp. (e.g., *Hordeum vulgare*), *Ipomoea batatas*, *Juglans* spp., *Lactuca sativa*, *Linum usitatissimum*, *Litchi chinensis*, *Lotus* spp., *Luffa acutangula*, *Lupinus* spp., *Lycopersicon* spp. (e.g., *Lycopersicon esculenturn*, *Lycopersicon lycopersicum*, *Lycopersicon pyriforme*), *Malus* spp., *Medicago sativa*, *Mentha* spp., *Miscanthus sinensis*, *Morus nigra*, *Musa* spp., *Nicotiana* spp., *Olea* spp., *Oryza* spp. (e.g., *Oryza sativa*, *Oryza latifolia*), *Panicum miliaceum*, *Panicum virgatum*, *Passiflora edulis*, *Petroselinum crispum*, *Phaseolus* spp., *Pinus* spp., *Pistacia vera*, *Pisum* spp., *Poa* spp., *Populus* spp., *Prunus* spp., *Pyrus communis*, *Quercus* spp., *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* spp., *Solanum* spp. (e.g., *Solanum tuberosum*, *Solanum integrifolium* or *Solanum lycopersicum*), *Sorghum bicolor*, *Sorghum halepense*, *Spinacia* spp., *Tamarindus indica*, *Theobroma cacao*, *Trifolium* spp., *Triticosecale rimpaui*, *Triticum* spp. (e.g., *Triticum aestivum*, *Triticum durum*, *Triticum turgidum*, *Triticum hybernum*, *Triticum macha*, *Triticum sativum* or *Triticum vulgare*), *Vaccinium* spp., *Vicia* spp., *Vigna* spp., *Viola odorata*, *Vitis* spp., and *Zea mays*. Especially preferred are rice, oilseed rape, canola, soybean, corn (maize), cotton, sugarcane, alfalfa, sorghum, and wheat.

In certain embodiments, the slurry comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 70%, 80%, 90%, 95%, 96%, 97%, 98% or 99% (w/w) of bentonite. In some embodiments the concentration of bentonite in the slurry is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 70%, 80%, 90%, 95%, 96%, 97%, 98% or 99% (w/w). Any of these values may be used to define a range for the concentration of bentonite in the slurry. For example the concentration of bentonite in the slurry may be from about 1% (w/w) to about 10% (w/w), or from about 10% (w/w) to about 50% (w/w), or from about 25% to about 75%.

In certain embodiments, the slurry comprises about 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, or 95% (w/w) of water. In some embodiments the concentration of water in the slurry is at least about 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, or 95% (w/w). Any of these values may be used to define a range for the concentration of water in the slurry. For example the concentration of water in the slurry may be from about 1% (w/w) to about 10% (w/w), or from about 10% (w/w) to about 50% (w/w).

In some embodiments the slurry is a saturated bentonite slurry based on the Swell Index of the bentonite. As used herein, the term "saturated slurry" or "saturated bentonite slurry" refers to a slurry which contains at least the amount of liquid required for complete saturation of the bentonite as determined by the Swell Index. For example, for a bentonite that has a Swell Index of 24 ml/2 g, about 12 ml of fluid are used per gram of bentonite to form a saturated slurry.

In some embodiments the slurry is a supersaturated slurry. As used herein, the term "supersaturated slurry" or "supersaturated bentonite slurry" refers to a slurry which contains more than the amount of liquid required for complete saturation of the bentonite as determined by the Swell Index. For example, for a bentonite that has a Swell Index of 24 ml/2 g, at least about 12 ml of fluid are used per gram of bentonite to form a supersaturated slurry.

In some embodiments, the slurry comprises a bentonite selected from the group consisting of a green bentonite, a white bentonite, an off-white bentonite, a red bentonite, or a brown bentonite.

The slurry comprising bentonite and water may further comprise a compound selected from the group consisting of a fertilizer, a plant growth regulator, a fungicide and an insecticide.

In a particular embodiment, the slurry comprising bentonite further comprises a compound selected from a fertilizer and a plant growth regulator. A fertilizer may comprise one or more of the elements important for plant growth, including, but not limited to, the macronutrients nitrogen (N), phosphorous (P), and potassium (K); the secondary macronutrients calcium (Ca), sulfur (S), and magnesium (Mg); and the micronutrients boron (B), chlorine (Cl), manganese (Mn), iron (Fe), zinc (Zn), copper (Cu), molybdenum (Mo), nickel (Ni), and cobalt (Co).

Sources of the elements important for plant growth are well known in the art and are described, for example, in US 2010/0267554. Substances that may be added to the slurry to provide nitrogen include, but are not limited to ammonium sulfate, ammonium nitrate, fish protein digest, ammonium phosphate sulfate, phosphate nitrate, diammonium phosphate, ammoniated single superphosphate, ammoniated triple superphosphate, nitric phosphates, ammonium chloride, calcium nitrate, calcium cyanamide, sodium nitrate, urea, urea-ammonium nitrate solution, nitrate of soda potash, potassium nitrate, and combinations thereof.

Phosphate compounds that may be added to the slurry include, but are not limited to, mono-potassium phosphate, superphosphate (single/double or triple), phosphoric acid, ammonium phosphate sulfate, ammonium phosphate nitrate, diammonium phosphate, ammoniated superphosphate (single, double or triple), nitric phosphates, potassium pyrophosphates, sodium pyrophosphate, and combinations thereof.

Potassium compounds that may be added to the slurry include, but are not limited to, mono-potassium phosphate, potassium chloride, potassium sulfate, potassium gluconate, sulfate of potash magnesia, potassium carbonate, potassium acetate, potassium citrate, potassium hydroxide, potassium manganate, potassium molybdate, potassium thiosulfate, potassium zinc sulfate, and combinations thereof.

Calcium containing materials that that may be added to the slurry include, but are not limited to, calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium propionate, calcium saccharate, calcium sulfate, calcium tartrate, and mixtures thereof.

Magnesium compounds that may be added to the slurry include, but are not limited to, magnesium sulfate, magnesium oxide, dolomite, magnesium acetate, magnesium benzoate, magnesium bisulfate, magnesium borate, magnesium chloride, magnesium citrate, magnesium nitrate, magnesium phosphate, magnesium salicylate, and combinations thereof. Sulfur compounds that may be added to the slurry include, but are not limited to, magnesium sulfate, ammonium phosphate sulfate; calcium sulfate, potassium sulfate, sulfuric acid, cobalt sulfate, copper sulfate, ferric sulfate, ferrous sulfate, sulfur, cysteine, methionine, and combinations thereof.

Zinc containing compounds that may be added to the slurry include, but are not limited to, chelated zinc, zinc sulfate, zinc oxide, zinc acetate, zinc benzoate, zinc chloride, zinc bis(dimethyldithiocarbamate), zinc citrate, zinc nitrate, zinc salicylate, and combinations thereof.

Iron containing compounds that may be added to the slurry include, but are not limited to, chelated iron, ferric chloride, ferric citrate, ferric fructose, ferric glycerophosphate, ferric nitrate, ferric oxide, ferrous chloride, ferrous citrate, ferrous fumarate, ferrous gluconate, and ferrous succinate, and combinations thereof.

Manganese compounds that may be added to the slurry include, but are not limited to, manganese sulfate, manganese acetate, manganese chloride, manganese nitrate, manganese phosphate, and combinations thereof.

Cobalt materials that may be added to the slurry include, but are not limited to, cyanocobalamin, cobaltic acetate, cobaltous chloride, cobaltous oxalate, cobaltous potassium sulfate, cobaltous sulfate, and combinations thereof.

In certain embodiments, the concentration of the one or more elements important for plant growth in the slurry is about 0.001, 0.005, 0.01, 0.05, 0.1, 0.5, 1, 5, 10, 25, 50, 75, 100, 125, 150, 175, 200, 225, 250, 275, 300, 325, 350, 375, 400, 425, 450, 475, 500, 600, 700, 800, 900, 1000, 2000, 3000, 4000, or 5000 ppm (w/w). In some embodiments, the concentration of the one or more elements important for plant growth in the slurry is at least about 0.001, 0.005, 0.01, 0.05, 0.1, 0.5, 1, 5, 10, 25, 50, 75, 100, 125, 150, 175, 200, 225, 250, 275, 300, 325, 350, 375, 400, 425, 450, 475, 500, 600, 700, 800, 900, 1000, 2000, 3000, 4000, or 5000 ppm (w/w). Any of these values may be used to define a range for the concentration of the element important for plant growth in the slurry. For example, the concentration of the element important for plant growth in the slurry may range from about 1 ppm (w/w) to about 1000 ppm (w/w), or from about 10 ppm (w/w) to about 100 ppm (w/w).

Plant growth regulators that may be added to the slurry comprising bentonite and water include, but are not limited to, auxins (e.g., indole-3-acetic acid (IAA), 1-naphthaleneacetic acid (NAA), and indole-3-butyric acid (IBA)), giberellins (e.g., ProGibb 4%), cytokinins, ethylene-related compounds (e.g., ethephon), abscisic acid, brassinosteroids, jasmonates, polyamines, and karrikins. In one embodiment of the invention, the plant growth regulator is IAA.

As used herein, the term "ethylene-related compounds" refers to compounds that release ethylene upon application to the plant (e.g. ethephon) or compounds that regulate ethylene sensitivity (e.g. silver thiosulfate (STS)).

Additional compounds that may be added to the slurry comprising bentonite and water include, but are not limited to, amino acids, peptides, proteins, and gene regulators (e.g. transcription and translation regulators).

In certain embodiments, the concentration of the plant growth regulator in the slurry is about 0.001, 0.005, 0.01, 0.05, 0.1, 0.5, 1, 5, 10, 25, 50, 75, 100, 125, 150, 175, 200, 225, 250, 275, 300, 325, 350, 375, 400, 425, 450, 475, 500, 600, 700, 800, 900, 1000, 2000, 3000, 4000, or 5000 ppm. In some embodiments, the concentration of the plant growth regulator in the slurry is at least about 0.001, 0.005, 0.01, 0.05, 0.1, 0.5, 1, 5, 10, 25, 50, 75, 100, 125, 150, 175, 200, 225, 250, 275, 300, 325, 350, 375, 400, 425, 450, 475, 500, 600, 700, 800, 900, 1000, 2000, 3000, 4000, or 5000 ppm. Any of these values may be used to define a range for the concentration of the plant growth regulator in the slurry. For example, the concentration of the plant growth regulator in the slurry may range from about 10 ppm to about 500 ppm, from about 1 ppm to about 25 ppm, or from about 0.1 ppm to about 10 ppm.

Fungicides that may be added to the slurry comprising bentonite and water include, but are not limited to, trifloxystrobin, metalaxyl, tebuconazole, imazalil, pyraclostrobin and ipconazole.

Insecticides that may be added to the slurry comprising bentonite and water include, but are not limited to, imidacloprid (e.g., MACHO 600ST, GAUCHO 600 FS), clothianidin (e.g., BELAY, PONCHO), terbufos (e.g., COUNTER), thiamethoxam (e g., CRUISER), clove, thyme and cinnamon oil (e.g., ECOTROL), tefluthrin (e.g., FORCE), chlorethoxyfos (e.g., FORTRESS), permethrin, and carboxin.

Microorganisms that enhance plant growth may also be added to the slurry. For example, *Rhizobium* inoculant may be added to the slurry to enhance nitrogen fixation in legumes.

The slurries may be prepared by adding powdered forms of bentonite to water and then mixing by hand or with an automated mixer. In some embodiments, additional compounds such as fertilizers, plant growth regulators, insecticides, and fungicides as described above may be mixed with the water before adding the powdered bentonite. In other embodiments, the powdered bentonite is first mixed with water and then additional compounds such as fertilizers, plant growth regulators, insecticides, and fungicides as described above may be added. Methods of preparing water-based slurries from clay powders are known in the art and are described, for example, in U.S. Pat. No. 8,691,052.

In certain aspects, the present invention relates to a method of enhancing a growth-related trait in a plant propagative material relative to a control plant propagative material, comprising applying a slurry comprising bentonite and water to a plant growth medium; and contacting a plant propagative material with the slurry in the plant growth medium, wherein a growth-related trait of the plant propagative material is enhanced relative to a control plant propagative material that is not treated with the slurry. In particular embodiments, the growth-related trait is enhanced under conditions of environmental stress, for example, drought conditions. In particular embodiments, the growth-related trait is enhanced in a crop that is not irrigated. In another embodiment, the growth-related trait is enhanced in a crop that relies on natural sources of water, e.g., rain.

In one embodiment, the slurry comprising bentonite and water may be applied using an automatic hopper and dispenser, which increases the speed of planting. In one embodiment, the slurry may be dispensed using mechanical methods, compression methods, air pressure methods, jet stream methods, gravity methods, centrifugal methods, metered pump methods, hydraulic methods, or other methods. In some embodiments, an applicator which is custom designed for application of the slurry may be used. For example, the slurry comprising bentonite and water may be applied using a custom designed applicator, for example, for bentonite embedded planting plugs, which increases the speed of planting.

The growth-related traits that may be enhanced by the methods of the present invention include, but are not limited to, total seed germination, rate of seed germination, plant biomass, disease tolerance, insect tolerance, herbivore tolerance (for example, tolerance to feeding by animals such as snails, rabbits, deer or groundhogs), drought tolerance, heat tolerance, cold tolerance, salinity tolerance, tolerance to heavy metals, total yield, seed yield, flowering time (e.g. early flowering time), root growth, early vigor, plant biomass, plant size, total plant dry weight, above-ground dry weight, above-ground fresh weight, leaf area, stem volume, plant height, rosette diameter, leaf length, root length, root mass, tiller number, and leaf number.

In particular embodiments, the growth-related trait is selected from the group consisting of total seed germination, rate of seed germination, plant biomass, insect tolerance, early flowering time, herbivore tolerance, and drought tolerance.

As used herein, the term "biomass" refers to the total weight of a plant. Within the definition of biomass, a distinction may be made between the biomass of one or more parts of a plant, which may include any one or more of the following: aboveground parts including, but not limited to, shoot biomass, seed biomass, leaf biomass; aboveground harvestable parts including, but not limited to, shoot biomass, seed biomass, leaf biomass; parts below ground, including, but not limited to, root biomass, tubers, bulbs; harvestable parts below ground, including, but not limited to, root biomass, tubers, bulbs; harvestable parts partially below ground including, but not limited to, beets and other hypocotyl areas of a plant, rhizomes, stolons or creeping rootstalks; vegetative biomass including, but not limited to, root biomass, shoot biomass; reproductive organs; and propagules including, but not limited to, seeds.

As used herein, the term "early flowering time" refers to a plant which begins to flower earlier than a control plant. Thus, this term refers to plants that show an earlier start of flowering. Flowering time of plants can be assessed by counting the number of days ("time to flower") between sowing and the emergence of a first inflorescence. The "flowering time" of a plant can for instance be determined using the method as described in WO07/093444, the entire contents of which are incorporated herein by reference.

As used herein, the term "drought conditions" refers to any stress which leads to a lack of water content in plants, a lack of water availability to plants, a lack of water uptake potential in plants, or a reduction in the water supply to plants. Specifically, a "drought" refers to a deficiency of precipitation resulting from a short term or long-term weather pattern. Drought conditions are determined easily by one of ordinary skill in the art. For example, the Palmer Drought Severity Index (PDSI), which is a measure of soil moisture, the Crop Moisture Index (CMI), and the Z index can be used to determine drought conditions.

Growth-related traits may be enhanced using the methods of the present invention. For example, in some embodiments, any of the growth-related traits described herein may be increased by at least about 5, 10, 15, 20, 25, 30, 35, 40, 45, 50, 55, 60, 65, 70, 75, 80, 85, 90, 95, 100, 150, 200, 300, 400, 500, 600, 700, 800, 900 or 1000% in a plant propagative material to which a slurry comprising bentonite and water has been applied relative to a control plant propagative material to which a bentonite/water slurry has not been applied.

For example, in some embodiments, total seed germination may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In one embodiment, total seed germination may be enhanced 2-fold in a plant propagative material to which a slurry comprising bentonite and water has been applied, as compared to a control plant propagative material to which a bentonite/water slurry has not been applied. In one embodiment, total seed germination may be enhanced 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

In a particular embodiment, the total seed germination is increased by at least 3-fold (for example, from 33% germination to at least 99% germination) under drought conditions. This level of increase in total seed germination under drought conditions can prevent crop failure due to drought and eliminate the need for replanting.

In another embodiment, the rate of seed germination may be decreased by 1 day in a plant propagative material to which a slurry comprising bentonite and water has been applied, as compared to a control plant propagative material to which a bentonite/water slurry has not been applied. In one embodiment, the rate of seed germination may be decreased by 0.5 days, 1 day, 1.5 days, 2 days, 3 days, 4 days, 5 days, 6 days, 7 days, 8 days, 9 days, 10 days or 14 days in a plant propagative material to which a slurry comprising bentonite and water has been applied, as compared to a control plant propagative material to which a bentonite/water slurry has not been applied.

In another embodiment, the percentage of seed germination may be increased by 10% in a plant propagative material to which a slurry comprising bentonite and water has been applied, as compared to a control plant propagative material to which a bentonite/water slurry has not been applied. In one embodiment, the percentage of seed germination may be increased by 10%, 15%, 20%, 25%, 30%, 35%, 40%, 45%, 50%, 55%, 60%, 65%, 70%, 75%, 80%, 85%, 90%, 95% or 100% in a plant propagative material to which a slurry comprising bentonite and water has been applied, as compared to a control plant propagative material to which a bentonite/water slurry has not been applied.

In another embodiment, plant biomass may be enhanced by at least about 5, 10, 15, 20, 25, 30, 35, 40, 45, 50, 55, 60, 65, 70, 75, 80, 85, 90, or 95% in a plant propagative material to which a slurry comprising bentonite and water has been applied, as compared to a control plant propagative material to which a bentonite/water slurry has not been applied. In some embodiments, plant biomass may be enhanced by at least about 2-fold in a plant propagative material to which a slurry comprising bentonite and water has been applied, as compared to a control plant propagative material to which a bentonite/water slurry has not been applied. In one embodiment, plant biomass may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

In some embodiments, insect tolerance may be enhanced by at least about 5, 10, 15, 20, 25, 30, 35, 40, 45, 50, 55, 60, 65, 70, 75, 80, 85, 90, or 95% in a plant propagative material to which a slurry comprising bentonite and water has been applied, as compared to a control plant propagative material to which a bentonite/water slurry has not been applied. In some embodiments, insect tolerance may be enhanced 2-fold in a plant propagative material to which a slurry comprising bentonite and water has been applied, as compared to a control plant propagative material to which a bentonite/water slurry has not been applied. In one embodiment, insect tolerance may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

Insect tolerance, disease tolerance and environmental stress tolerance (e.g., drought tolerance) may be measured by measuring any of the growth related traits described herein. For example, drought tolerance may be determined by measuring percent germination, rate of germination, plant biomass, yield, or seed yield under drought conditions. The insect tolerance, disease tolerance, or environmental stress tolerance may be quantified by measuring the growth-related trait under the appropriate conditions. For example, a plant propagative material treated with a slurry comprising bentonite and water that exhibited a 10% increase in yield relative to a plant propagative material that was not treated with the slurry would be determined to exhibit a 10% increase in drought tolerance. As another example, a plant propagative material treated with a slurry comprising bentonite and water that exhibited a 10% increase in the rate of leaf out, as compared to a plant propagative material that was not treated with the slurry would be determined to exhibit a 10% increase in insect tolerance. A plant propagative material with increased rate of leaf out is more resistant to insect infestation or attack.

In some embodiments, disease tolerance or herbivore tolerance may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In another embodiment, disease tolerance or herbivore tolerance may be enhanced 2-fold in a plant propagative material to which a slurry comprising bentonite and water has been applied, as compared to a control plant propagative material to which a bentonite/water slurry has not been applied. In one embodiment, disease tolerance or herbivore tolerance may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

In some embodiments, drought tolerance may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In some embodiments, drought tolerance may be enhanced 2-fold in a plant propagative material to which a slurry comprising bentonite and water has been applied, as compared to a control plant propagative material to which a bentonite/water slurry has not been applied. In one embodiment, drought tolerance may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

In some embodiments, heat tolerance or cold tolerance may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In some embodiments, heat tolerance or cold tolerance may be enhanced 2-fold in a plant propagative material to which a slurry comprising bentonite and water has been applied, as compared to a control plant propagative material to which a bentonite/water slurry has not been applied. In one embodiment, heat tolerance or cold tolerance may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

In some embodiments, salinity tolerance or tolerance to heavy metals may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In some embodiments, salinity tolerance or tolerance to heavy metals may be enhanced 2-fold in a plant propagative material to which a slurry comprising bentonite and water has been applied, as compared to a control plant propagative material to which a bentonite/water slurry has not been applied. In one embodiment, salinity tolerance or tolerance to heavy metals may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied. Salinity tolerance or tolerance to heavy metals may be determined using standard methods in the art. For example, salinity may be determined by measuring the exchange of cations, e.g., calcic to sodic.

In some embodiments, total yield may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In some embodiments, total yield may be enhanced 2-fold in a plant propagative material to which a slurry comprising bentonite and water has been applied, as compared to a control plant propagative material to which a bentonite/water slurry has not been applied. In one embodiment, total yield may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied. In one embodiment of the invention, at least 75% of the total number of seeds to which a bentonite/water slurry are applied germinate. In another embodiment, at least 80%, 85%, 90%, 95%, or 100% of the total number of seeds to which a bentonite/water slurry are applied germinate.

In some embodiments, root growth, early vigor, plant size, total plant dry weight, above-ground dry weight, above-ground fresh weight, leaf area, stem volume, plant height, rosette diameter, leaf length, root length, root mass, tiller number, or leaf number may be increased by at least about 5, 10, 15, 20, 25, 30, 35, 40, 45, 50, 55, 60, 65, 70, 75, 80, 85, 90, or 95% in a plant propagative material to which a slurry comprising bentonite and water has been applied relative to a control plant propagative material to which a bentonite/water slurry has not been applied. In some embodiments, root growth, early vigor, plant size, total plant dry weight, above-ground dry weight, above-ground fresh weight, leaf area, stem volume, plant height, rosette diameter, leaf length, root length, root mass, tiller number, or leaf number may be enhanced 2-fold in a plant propagative material to which a slurry comprising bentonite and water has been applied, as compared to a control plant propagative material to which a bentonite/water slurry has not been applied. In one embodiment, root growth, early vigor, plant size, total plant dry weight, above-ground dry weight, above-ground fresh weight, leaf area, stem volume, plant height, rosette diameter, leaf length, root length, root mass, tiller number, or leaf number may be enhanced 1.5-fold, 2-fold, 3-fold, 4-fold, 5-fold, 6-fold, 7-fold, 8-fold, 9-fold or 10-fold in a plant propagative material to which a slurry comprising bentonite and water has been applied, as compared to a control plant propagative material to which a bentonite/water slurry has not been applied.

Generally, an "enhanced growth-related trait" or an "increase in a growth-related trait" refers to a level of the trait in a test plant propagative material that is greater than the standard error of the assay employed to assess the level of the trait, and is preferably at least twice, and more preferably three, four, five or ten times the level of the trait in a control sample (e.g., sample of a plant propagative material that has not been contacted with a bentonite/water slurry) and preferably, the average expression level of the trait in several control samples.

Values and ranges included and/or intermediate within the ranges set forth herein are also intended to be within the scope of the present disclosure. Ranges having values recited herein as an upper or lower limit are also intended to be within the scope of the present disclosure.

Unlike seed coating, the water-based slurry comprising bentonite immediately introduces a long lasting hydrated microcosm that induces seed germination. For example, the slurry provides a hydrated microenvironment to the seed that keeps the seed shell moist and promotes water absorption into the shell. This in turn allows the shell to swell and eventually crack and initiate germination. Intermittent drought stress is mitigated, as the slurry volume maintains a hydrated environment to promote seed shell swelling and germination. Bentonite is extremely hygroscopic and will not release water easily to the surrounding soil. Plant propagative materials, however, such as seeds, are porous. Thus, when surrounded by a bentonite slurry of the invention, the bentonite provides a hydrated microcosm for the plant propagative material, and capillary action draws water into the seed shell, which induces seed germination. Once the seed shell has swollen and cracked, plant growth regulators and fertilizer in the slurry can enhance germination and rooting activity and expedite emergence of the seedling from the soil and early growth of the developing seedling. In one embodiment, the slurry comprising bentonite and water, along with a plant propagative material (for example, a seed) may be applied to a plant growth medium (for example, a soil) using an automatic hopper and dispenser, which increases the speed of planting.

In certain embodiments, the growth related trait is enhanced under unfavorable environmental conditions, including, but not limited to, drought conditions, high salinity conditions, cold stress conditions and heat stress conditions. As used herein, the term "drought conditions" refer to conditions under which a region receives a deficiency in its water supply, whether atmospheric, surface, or ground water. Due to the hydrated microenvironment that the slurry provides, the slurry is particularly well suited for enhancing growth-related traits under drought conditions or under conditions of high salinity. The slurry may also enhance growth-related traits under other environmental stress conditions, such as high or low temperature conditions. For example, the positive effects of the slurry on germination and growth of the seedling may counteract negative effects caused by unfavorable temperatures.

In some embodiments, the slurry is added to the plant growth medium before planting the plant propagative material. For example, in some embodiments, the slurry is applied to the plant growth medium (for example, a soil) and the plant propagative material (for example, a seed) is then introduced into the plant growth medium after the slurry has been applied. In some embodiments, the plant propagative material (for example, a seed) is placed in direct contact with the slurry which has been added to the plant growth medium (for example, a soil). For example, for seed planting, a drop of the slurry may be introduced into the planting hole and the seed may then be placed in contact with the slurry. The hole containing the seed and the slurry may then be covered with additional plant growth medium.

In one embodiment, the slurry comprising bentonite and water, along with a plant propagative material (for example, a seed) may be applied to a plant growth medium (for example, a soil) using an automatic hopper and dispenser, which increases the speed of planting. In one embodiment, the slurry and the plant propagative material may be applied to a plant growth medium at the same time using an automatic hopper and dispenser. In another embodiment, the slurry and the plant propagative material may be applied sequentially to a plant growth medium using an automatic hopper and dispenser. For example, an automatic hopper and dispenser may be used to first apply the slurry, followed by the plant propagative material. Alternatively, an automatic hopper and dispenser may be used to first apply the seed, followed by the slurry.

For transplanting (e.g., vegetable transplants, flower transplants, trees, or shrubs) the slurry may be applied to a hole in the plant growth medium (e.g., soil) and the transplant may then be applied to the hole containing the slurry. The slurry may also be mixed into the plant growth medium before the plant propagative material is planted. For example, for field production, the slurry may be broadcast in the field and mixed into the soil before seeds or transplants are planted. In other embodiments, the slurry is not mixed into the plant growth medium before the plant propagative material is introduced into the medium. The slurry may be applied to the plant growth medium manually or using equipment such as a spreader or planter, followed by application of the plant propagative material.

In some embodiments, the slurry is applied to discrete areas of a field in which the plant propagative material will be planted, such as a planting hole or a planting row, and is not broadcast across the field. Discrete application of the slurry to the planting area reduces the amount of slurry needed and prevents changes to the composition of the soil that may occur with broadcasting of bentonite. In certain embodiments, the slurry is applied to the planting medium at a rate of less than about 1000, 900, 800, 700, 600, 500, 400, 300, 200, 100, 90, 80, 70, 60, 50, 40, 30, 20 or 10 kg/acre. Any of these values may be used to define a range for the amount of the slurry that is applied to the field. For example, the slurry may be applied to the field at a rate from about 100 to about 1000 kg/acre, from about 50 to about 500 kg/acre, or from about 10 to about 100 kg/acre.

In certain embodiments, the slurry is applied to less than 90%, 80%, 70%, 60%, 50%, 40%, 30%, 20%, 10%, 9%, 8%, 7%, 6%, 5%, 4%, 3%, 2% or 1% of the surface area of the plant growth medium, for example the surface area of a field.

In some embodiments the slurry is applied to the plant propagative material before the plant propagative material is introduced into the plant growth medium. For example, seeds may be mixed with the slurry to form a seed/slurry mixture, and this mixture may be applied to the plant growth medium. In one embodiment, the seed/slurry mixture may be applied to the plant growth medium using an automatic hopper and dispenser. In some embodiments, the slurry is applied to the roots of a seedling or transplant, for example by dipping or submerging the roots of the plant into the slurry, and the treated seedling or transplant is then introduced into the plant growth medium. In some embodiments, for example for gardening or landscaping applications, the mixture of the slurry and plant propagative material is applied to the plant growth medium manually. In some embodiments, for example, for large-scale crop production, the mixture of the slurry and the plant propagative material is applied in the field using commercially available planters or spreaders, such as automated transplanters used for vegetable production or seed planters used in no-till farming systems. For automated seed planting, a mixture of seed and slurry may be added to the seed hopper of a seed planter.

In one embodiment, the slurry comprising bentonite and water may be applied using an automatic hopper and dispenser, which increases the speed of planting. In one embodiment, the slurry may be dispensed using mechanical methods, compression methods, air pressure methods, jet stream methods, gravity methods, centrifugal methods, metered pump methods, hydraulic methods, or other methods. In some embodiments, an applicator which is custom designed for application of the slurry may be used. For example, the slurry comprising bentonite and water may be applied using a custom designed applicator, for example, for bentonite embedded planting plugs, which increases the speed of planting.

The slurry comprising bentonite and water may also be applied using an industrial fertilizer applicator under intermittent pressure to apply discrete amounts of the slurry to the planting hole, or under constant pressure to apply a stream of the slurry to a seed row. Fertilizer applicators are commercially available, for example, from John Deere (Moline, Ill.).

The slurry or seed/slurry mixture may also be applied to a plant growth medium contained in a pot, for example a pot comprising peat moss or a synthetic plant growth medium. In some embodiments, the slurry comprising bentonite and water is incorporated into a preformed planting container for plug production comprising peat moss and optionally other plant growth medium. Preformed planting containers comprising peat moss for plug production are commercially available, for example, from Grow-Tech LLC (South Portland, Me.).

As used herein, the term "plant growth medium" refers to a medium that is capable of supporting a plant, including but not limited to, field soil, potting soil, perlite, vermiculite, peat moss, mineral wool, compost, or mixtures thereof. In one embodiment, the plant growth medium is soil. In another embodiment, the plant growth medium is field soil.

In some embodiments, the slurry comprising bentonite and water is applied to a plug, e.g., a seedling grown in a tray (e.g., an expanded polystyrene or polythene tray) filled with growth medium. The slurry may be applied to the plug by dipping the roots of the plug into a bentonite slurry of the invention or by flooding or soaking the tray in which the plug is grown with the bentonite slurry. Once the plug is treated with the bentonite slurry of the invention, the treated plugs may be planted in a field or in a controlled growth environment. In another embodiment, the slurry comprising bentonite and water is applied to a plug, e.g., a seed grown in a tray (e.g., an expanded polystyrene or polythene tray) filled with growth medium. Once the plug is treated with the bentonite slurry of the invention, the treated plugs may be planted in a field or in a controlled growth environment. Alternatively, a plant growth medium, such as a seed, may be inserted mechanically into a bentonite peat (or peat similar) plug, and then planted in soil or a pot manually or using machines.

In a particular embodiment, the treated plug is grown under broad spectrum LED lighting using a hydroponic system. In a preferred embodiment, the plug is an herb, for example, basil, parsley, or cilantro. In some embodiments, the seed planted into the tray for production of the plug may also be treated with slurry by the methods described herein. For example, the slurry may be added to the growth medium before planting the seed, or the seed may be treated with the slurry before planting.

The slurry of the present invention may also be used in land reclamation, for example, after afforestation, to improve the survival and growth of plants such as grass or trees under unfavorable environmental conditions such as poor soil quality, flooding or drought. Accordingly, in one embodiment, the invention provides methods for promoting reforestation comprising applying a slurry comprising bentonite and water to the soil. For reforestation, the slurry comprising bentonite and water may be applied by dipping the roots of a tree sapling or grass into the slurry before planting. Alternatively, the slurry comprising bentonite and water may be applied to a plant growth medium, followed by introduction of a plant propagative material into the plant growth medium containing the slurry.

In some aspects, the present invention relates to methods of remediating soil contaminated by heavy metal ions or other pollutants by applying any of the aforementioned slurries comprising water and bentonite to the contaminated soil.

In some embodiments, the bentonite may be applied to discrete areas of the plant growth medium without formation of a slurry. For example, the bentonite may be applied to discrete areas of the plant growth medium (e.g., a planting hole or planting row) in the form of a dry powder. Water or a fertilizer may then be added to the plant growth medium to hydrate the bentonite.

In some aspects, the present invention relates to a method of enhancing a growth-related trait in a plant propagative material relative to a control plant propagative material, comprising a) applying bentonite to a discrete area of a plant growth medium; and b) introducing the plant propagative material into the discrete area of the plant growth medium containing the bentonite,
wherein the growth-related trait of the plant propagative material is enhanced relative to a control plant propagative material that is not treated with the bentonite.

Any of the methods described above for applying a slurry to the plant growth medium may also be used to apply the dry bentonite to a discrete area of the plant growth medium.

In certain embodiments, the bentonite is applied to the planting medium at a rate of less than about 1000, 900, 800, 700, 600, 500, 400, 300, 200, 100, 90, 80, 70, 60, 50, 40, 30, 20 or 10 kg/acre. Any of these values may be used to define a range for the amount of the slurry that is applied to the field. For example, the slurry may be applied to the field at a rate from about 100 to about 1000 kg/acre, from about 50 to about 500 kg/acre, or from about 10 to about 100 kg/acre.

In certain embodiments, the bentonite is applied to less than 90%, 80%, 70%, 60%, 50%, 40%, 30%, 20%, 10%, 9%, 8%, 7%, 6%, 5%, 4%, 3%, 2% or 1% of the surface area of the plant growth medium, for example the surface area of a field.

The present invention is further defined in the following Example. It should be understood that this Example, while indicating preferred embodiments of the invention, is given by way of illustration only.

EXAMPLES

Example 1—Effect of Bentonite, Indole-3-Acetic Acid (IAA) and Fertilizer on Sunflower Seed Germination and Growth Under Water Stress Sunflower seeds (cultivar 'Mammoth', W. Atlee Burpee & Co., Warminster, Pa.) of equal size and uniformity were chosen. Seeds with cracks were discarded. The seeds were planted into uniform store bought potting soil which did not contain growth promoters. Seven treatment groups were evaluated:
1) control, potting soil only without bentonite;
2) green bentonite slurry;
3) white bentonite slurry;
4) green bentonite/IAA (indole-3-acetic acid) slurry;
5) white bentonite/IAA slurry;
6) green bentonite/fertilizer slurry;
7) white bentonite/fertilizer slurry.

Treatment groups 1-5 contained 6 pots each with one seed per pot. Treatment groups 6 and 7 contained 3 pots each with one seed per pot. White bentonite and green bentonite slurries (treatment groups 2 and 3) were prepared with water. Sufficient water was added to form a supersaturated slurry. For example, more than 24 ml of water was added per 2 grams of bentonite, and the bentonite was allowed to saturate over 12 hours with periodic stirring. After 12 hours, the slurry had settled to the bottom of the container with excess water pooled on top of the slurry. The excess water was poured off. The bentonite/IAA slurries (treatment groups 4 and 5) were prepared as described above, except that IAA powder was added to the bentonite before adding the water to produce a final concentration of 200 ppm IAA in the slurry. The bentonite/fertilizer slurry was prepared as described above except that fertilizer solution was mixed with the bentonite instead of water. The fertilizer used was MIRACLE-GRO (Scotts Miracle-Gro Company, Marysville, Ohio) at the manufacturer's recommended concentration of 1 tablespoon MIRACLE-GRO fertilizer per gallon of water. The concentration of plant nutrients in the diluted fertilizer solution is shown in Table 1 below.

TABLE 3

Concentration of plant nutrients in fertilizer solution added to slurry

| Nutrient | Concentration (ppm) |
| --- | --- |
| Nitrogen | 937.5 |
| Potassium | 312.5 |
| Phosphorous | 625 |
| Boron | 0.78 |
| Copper | 2.73 |
| Iron | 5.85 |
| Manganese | 1.95 |
| Molybdenum | 0.02 |
| Zinc | 2.34 |

Holes were made in the potting soil at equal measured depths and a drop (about 2 ml) of the slurry at least twice the size of the seed was added to the planting hole with a syringe. See FIG. 1. Each sunflower seed was embedded into the middle of the drop of slurry and covered with soil.

The seedlings were grown under water stress conditions to determine the effect of the bentonite slurry during drought stress. After planting, the potting soil was watered uniformly until complete saturation and then was not watered for four days until the soil was completely dry. After four days the soil was watered lightly and then allowed to dry completely with no watering for another 4 days. This 4 day watering cycle of light watering followed by 4 days of no watering was repeated throughout the course of the study.

Results

Bentonite had a positive effect on seed germination and plant growth under water stress conditions.

For example, the seeds treated with bentonite, either alone or in combination with fertilizer or IAA, germinated in 5-7 days and exhibited 100% germination, while the control seeds which were not treated with bentonite germinated in 12-15 days and exhibited only 33% germination. Thus the bentonite treatment increased both the rate of germination and the total percentage of germination under water stress conditions.

In addition, plants treated with bentonite exhibited accelerated growth, were larger, and had more robust stem and leaf development relative to the control plants. For example, some of the seedlings emerged from the soil but failed to "leaf out", i.e., develop cotyledons and/or true leaves. As shown in Table 2 below, the plants treated with bentonite exhibited a higher percentage of leaf out than the control plants. It was also observed that the control plants were more susceptible to damage by snails, possibly due to their slower growth rates. Thus the more rapid early growth of seeds treated with bentonite can also improve tolerance to herbivory by animals and insects that prey on newly germinating seeds.

TABLE 4

Germination and growth of sunflower seedlings with our without treatment with bentonite, IAA, or fertilizer.
Treatment groups 1-7 are described above.

| | Treatment Group | | | | | | |
|---|---|---|---|---|---|---|---|
| | 1 | 2 | 3 | 4 | 5 | 6 | 7 |
| Percent total germination | 33% | 100% | 100% | 100% | 100% | 100% | 100% |
| Days to germination | 7-12 | 5-7 | 5-7 | 5-7 | 5-7 | 5-7 | 5-7 |
| Percent leaf out | 33% | 100% | 50% | 100% | 83% | 100% | 100% |

Example 2—Effect of Bentonite on Sunflower Seed Germination and Soil Moisture Retention Sunflower seeds (cultivar 'Mammoth', W. Atlee Burpee & Co., Warminster, Pa.) of equal size and uniformity were chosen. Seeds with cracks were discarded. The seeds were planted into uniform store bought potting soil which did not contain growth promoters. Two treatment groups were evaluated:
1) potting soil only without bentonite (control); and
2) bentonite slurry.

Figure 6A:
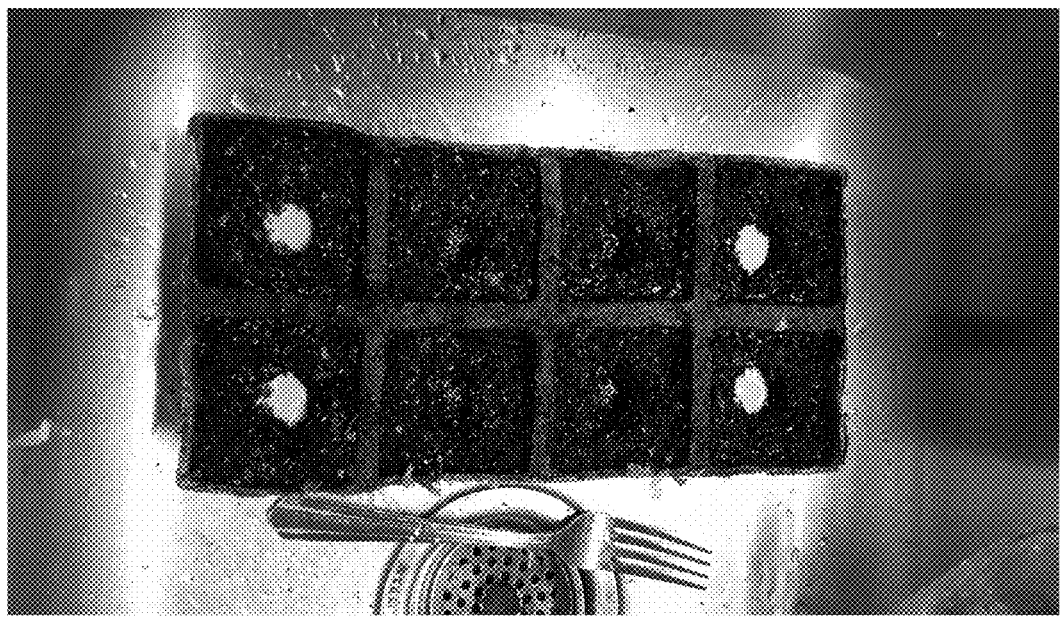
FIG. 6A shows slurry comprising bentonite and water placed in the planting holes in potting soil before planting of sunflower seeds.
Figure 6B:
FIG. 6B shows sunflower seedlings approximately 10 days after planting.

The bentonite slurry was prepared with distilled water as described above in Example 1. No fertilizer or growth hormone was added to the slurry. The seeds were planted into trays containing 8 pots (see FIGS. 6A and 6B). Each pot was filled halfway with potting soil, an indentation was made in the potting soil, and the indentation was filled with approximately 1 ml of bentonite slurry. One seed was then inserted into the bentonite slurry, and the pots were filled with potting soil and watered to saturation. The seedlings were grown under drought stress conditions by watering the pots every four days and allowing the potting soil to dry thoroughly between waterings. The seedlings were grown indoors with exposure to natural light. Germination was measured daily until all seeds had germinated. As shown in Table 5 below, seeds treated with the bentonite slurry exhibited an average total percent germination of 85% under drought stress conditions compared to an average total percent germination of 36% for the seeds that were not treated with bentonite.

TABLE 5

Percent germination of sunflower seeds with and without bentonite.
Each replicate contained four pots with bentonite slurry
and soil and four pots with soil alone (control).

| | % germination | |
|---|---|---|
| Replicate | bentonite + soil | soil |
| 1 | 83% | 33% |
| 2 | 100% | 25% |
| 3 | 50% | 33% |
| 4 | 75% | 25% |
| 5 | 100% | 50% |
| 6 | 75% | 25% |
| 7 | 100% | 25% |
| 8 | 83% | 25% |
| 9 | 100% | 50% |
| 10 | 100% | 25% |
| 11 | 75% | 25% |
| 12 | 83% | 33% |
| 13 | 100% | 50% |
| 14 | 83% | 33% |
| 15 | 100% | 25% |
| 16 | 75% | 25% |
| 17 | 100% | 25% |
| 18 | 100% | 75% |
| 19 | 75% | 25% |
| 20 | 75% | 25% |
| 21 | 100% | 20% |
| 22 | 100% | 50% |
| 23 | 75% | 25% |
| 24 | 100% | 75% |
| 25 | 50% | 50% |
| 26 | 75% | 25% |
| 27 | 100% | 50% |
| 28 | 50% | 50% |
| 29 | 100% | 50% |
| 30 | 75% | 25% |
| Average % Germination | 85% | 36% |
| Number of containers | n = 120 | n = 120 |

In addition, the seeds treated with bentonite slurry germinated more rapidly than seeds that were not treated with bentonite. For example, as shown in Table 6 below, 97% of the replicates treated with bentonite slurry had at least one seed that germinated in 5-7 days, while only 7% of the replicates containing control seeds grown in soil alone had at least one seed that germinated in this time period. Thus treatment with bentonite slurry increased both total germination and the rate of germination under drought stress conditions.

TABLE 6

Days to germination of sunflower seeds with and without bentonite.
Each replicate contained four pots with bentonite slurry and
soil and four pots with soil alone (control). Percentages reflect
the number of replicates that contained at least one seed that
germinated within the indicated time period.

| | Time to germinate | | |
|---|---|---|---|
| Replicate | 5-7 days | 8-12 days | > than 12 |
| 1 | x | + | |
| 2 | x | + | |
| 3 | x | + | |
| 4 | x | x + | + |
| 5 | x | + | |
| 6 | x | + | |
| 7 | x | | + |
| 8 | | x + | + |
| 9 | x | x + | |
| 10 | x | + | |
| 11 | x | | + |
| 12 | x | + | |
| 13 | x | + | |
| 14 | x | x + | + |
| 15 | x | | + |
| 16 | x | + | |
| 17 | x | | + |
| 18 | x + | + | |
| 19 | x | + | + |

TABLE 6-continued

Days to germination of sunflower seeds with and without bentonite. Each replicate contained four pots with bentonite slurry and soil and four pots with soil alone (control). Percentages reflect the number of replicates that contained at least one seed that germinated within the indicated time period.

| Replicate | Time to germinate | | |
|---|---|---|---|
| | 5-7 days | 8-12 days | > than 12 |
| 20 | x | x + | |
| 21 | x | + | + |
| 22 | x | + | |
| 23 | x | | + |
| 24 | x | + | |
| 25 | x | x + | |
| 26 | x | + | |
| 27 | x | | + |
| 28 | x + | x + | |
| 29 | x | + | + |
| 30 | x | + | + |
| | bentonite + soil: 97% | bentonite + soil: 23% | bentonite + soil: 0% |
| | soil alone: 7% | soil alone: 80% | soil alone: 43% |

"x" indicates bentonite + soil and "+" indicates soil alone (control).

Example 3—Moisture Retention of a Bentonite Slurry Plug in Potting Medium

The moisture retention abilities of a bentonite slurry plug embedded in potting soil was determined. Three treatment groups were evaluated:

1. Wetted soil+bentonite slurry;
2. Wetted soil without bentonite (control); and
3. Non-wetted soil without bentonite (control).

Figure 7:
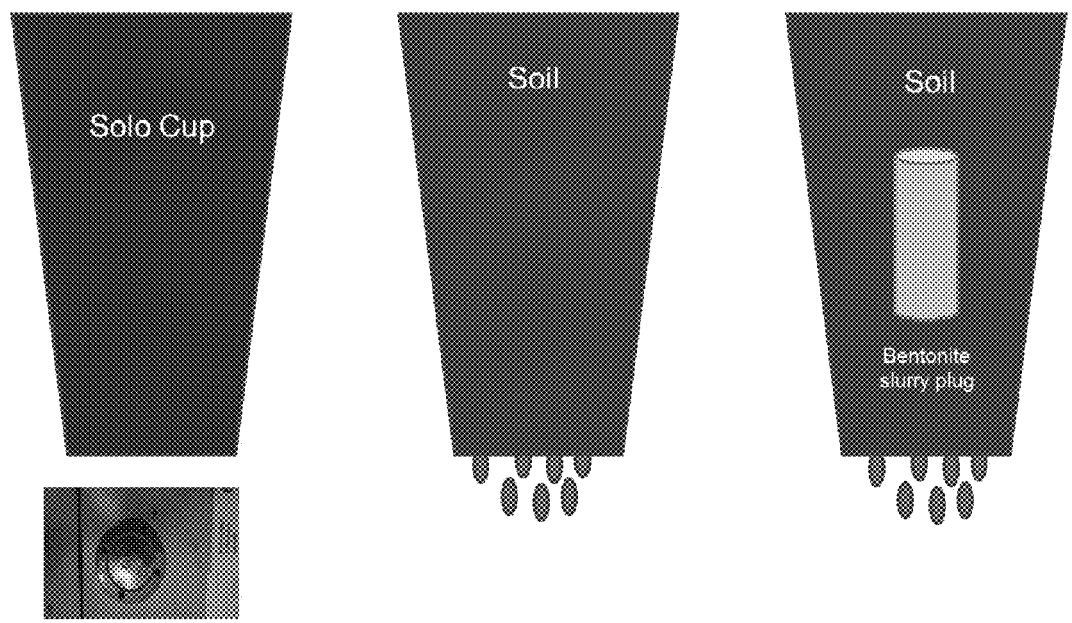
FIG. 7 shows a diagram of the cups filled with potting soil for measurement of water retention ability of the bentonite slurry.

The bentonite slurry was prepared with distilled water as described above in Example 1. Four holes were made in the bottom of a plastic cup for drainage. Screened commercially available potting soil that did not contain vermiculite was used for all treatment groups. For the wetted soil+bentonite slurry treatment group, the plastic cups were filled approximately halfway with potting soil, and an indentation was made in the potting soil. The indentation was filled with approximately 10 ml of bentonite slurry to form a bentonite slurry plug embedded in the potting soil. See FIG. 7. The cup was then filled with potting soil and watered to saturation. For the control groups, cups were filled with potting soil without adding bentonite slurry. For the wetted soil control, cups were watered to saturation. No water was added to the non-wetted soil control. The cups were not watered again throughout the course of the experiment. The cups were stored indoors at room temperature. The percent soil moisture was measured daily for 30 days using an HSM50 soil moisture meter (Omega, Stamford, Conn.). For the bentonite slurry+soil treatment group, the soil moisture meter probe was inserted into the bentonite slurry plug for measurement of moisture levels. As shown in Tables 7 and 8 below, the bentonite slurry embedded in wetted potting soil maintained a higher moisture content than wetted soil alone or the non-wetted potting soil control throughout the course of the experiment. These results demonstrate the water retention properties of the bentonite slurry.

TABLE 7

Moisture retention in potting medium with our without bentonite. Values are percent soil moisture and are an average of three measurements.

| Day | Non Wetted Soil Control | Wetted Bentonite + Soil | Wetted Soil |
|---|---|---|---|
| 1 | 9.7 | 22.7 | 22.3 |
| 2 | 9.6 | 22.6 | 22.1 |
| 3 | 9.5 | 22.5 | 21.7 |
| 4 | 9.4 | 22.2 | 21.3 |
| 5 | 9.3 | 22.0 | 20.3 |
| 6 | 9.1 | 21.7 | 19.8 |
| 7 | 9.0 | 21.4 | 19.4 |
| 8 | 8.7 | 21.2 | 19.1 |
| 9 | 8.8 | 20.9 | 18.6 |
| 10 | 8.4 | 20.7 | 17.7 |
| 11 | 8.2 | 20.6 | 17.2 |
| 12 | 7.9 | 20.4 | 17.1 |
| 13 | 7.9 | 20.3 | 16.9 |
| 14 | 7.6 | 20.0 | 16.4 |
| 15 | 7.5 | 19.9 | 16.0 |
| 16 | 7.1 | 19.9 | 15.6 |
| 17 | 6.9 | 19.7 | 15.2 |
| 18 | 6.8 | 19.7 | 14.8 |
| 19 | 6.7 | 19.6 | 14.5 |
| 20 | 6.5 | 19.5 | 14.1 |
| 21 | 6.2 | 19.4 | 13.9 |
| 22 | 6.1 | 19.3 | 13.5 |
| 23 | 6.0 | 19.3 | 13.1 |
| 24 | 5.7 | 19.1 | 13.0 |
| 25 | 5.6 | 18.9 | 12.6 |
| 26 | 5.5 | 18.8 | 12.2 |
| 27 | 5.4 | 18.6 | 11.9 |
| 28 | 5.3 | 18.5 | 11.7 |
| 29 | 5.2 | 18.4 | 11.6 |
| 30 | 5.0 | 18.2 | 11.3 |

TABLE 8

Average soil moisture retention in soil with our without bentonite slurry.

| | Non Wetted Soil Control | Wetted Bentonite Soil | Wetted Soil |
|---|---|---|---|
| AVERAGES –Day 1 | 9.7 | 22.7 | 22.3 |
| AVERAGES Day 30 | 5.0 | 18.2 | 11.3 |
| Change in Soil Moisture Content | 4.7 | 4.5 | 11.0 |
| % Moisture Retention | 52% | 80% | 51% |

I claim:

1. A method of enhancing germination of a seed relative to a control seed, comprising:
   a) applying a flowable supersaturated bentonite slurry comprising from about 1% to about 50% w/w of bentonite and at least about 50% w/w of water into a hole formed in a plant growth medium to form a supersaturated bentonite slurry plug, wherein the supersaturated bentonite slurry contains more than the amount of water required for complete saturation of the bentonite as determined by the Swell Index, and the bentonite is completely saturated with the water;
   b) introducing a seed into the hole formed in the plant growth medium containing the supersaturated bentonite slurry plug such that the seed is in contact with the supersaturated bentonite slurry plug; and
   (c) covering the seed and the supersaturated bentonite slurry plug with additional plant growth medium such that the supersaturated bentonite slurry plug is fully embedded within the plant growth medium, and (d) allowing the seed to germinate and grow, wherein the supersaturated bentonite slurry plug retains a higher moisture content than wetted soil alone such that germination of the seed is measurably enhanced relative to a control seed planted in growth medium alone that is not treated with the supersaturated bentonite slurry plug.

2. The method of claim 1, wherein the germination of the seed is determined by a measurement selected from the group consisting of total seed germination and rate of seed germination.

3. The method of claim 2, wherein total germination of the seed is increased by at least about 50% under drought conditions relative to a seed that is not treated with the supersaturated bentonite slurry plug.

4. The method of claim 2, wherein total germination of the seed is increased by at least 3-fold under drought conditions relative to a seed that is not treated with the supersaturated bentonite slurry plug.

5. The method of claim 2, wherein the rate of germination of the seed is decreased by at least 2 days under drought conditions relative to a seed that is not treated with the supersaturated bentonite slurry plug.

6. The method of claim 1, wherein the germination of the seed grown in contact with the bentonite slurry plug is enhanced under drought conditions.

7. The method of claim 1, wherein the supersaturated bentonite slurry plug further comprises at least one compound selected from the group consisting of a fertilizer, a plant growth regulator, a fungicide, an insecticide, an amino acid, a peptide, a protein, and a nucleic acid.

8. The method of claim 7, wherein the plant growth regulator is selected from the group consisting of auxins, giberellins, cytokinins, ethylene-related compounds, abscisic acid, brassinosteroids, jasmonates, polyamines, karrikins, and any combination thereof.

9. The method of claim 7, wherein the fertilizer comprises a micronutrient.

10. The method of claim 1, wherein the bentonite of the supersaturated bentonite slurry plug is selected from the group consisting of sodium bentonite and calcium bentonite.

11. The method of claim 1, wherein the supersaturated bentonite slurry plug is in contact with less than 10% of the surface of the plant growth medium.

12. The method of claim 1, wherein the supersaturated bentonite slurry comprises at least about 50% w/w of water and from about 10% to about 50% w/w of bentonite.

13. The method of claim 1, wherein the supersaturated bentonite slurry plug is at least twice the size of the seed.

14. The method of claim 1, wherein the supersaturated bentonite slurry plug comprises from about 5% to about 20% w/w of bentonite.

15. The method of claim 1, wherein the supersaturated bentonite slurry plug is applied to less than 5% of the surface of the plant growth medium.

16. The method of claim 1, wherein the plant growth medium is soil.

17. A method of enhancing germination of a seed relative to a control seed, comprising:
a) introducing a seed into a hole formed in a plant growth medium;
b) applying a flowable supersaturated bentonite slurry comprising from about 1% to about 50% w/w of bentonite and at least about 50% w/w of water into the hole formed in the plant growth medium to form a supersaturated bentonite slurry plug, such that the seed is in contact with the supersaturated bentonite slurry plug, wherein the supersaturated bentonite slurry contains more than the amount of water required for complete saturation of the bentonite as determined by the Swell Index, and the bentonite is completely saturated with the water;
(c) covering the seed and the supersaturated bentonite slurry plug with additional plant growth medium such that the supersaturated bentonite slurry plug is fully embedded within the plant growth medium; and
(d) allowing the seed to germinate and grow, wherein the supersaturated bentonite slurry plug retains a higher moisture content than wetted soil alone such that germination of the seed is measurably enhanced relative to a control seed planted in growth medium alone that is not treated with the supersaturated bentonite slurry plug.

18. The method of claim 17, wherein the germination of the seed is determined by a measurement selected from the group consisting of total seed germination and rate of seed germination.

19. The method of claim 18, wherein total germination of the seed is increased by at least about 50% under drought conditions relative to a seed that is not treated with the supersaturated bentonite slurry plug.

20. The method of claim 18, wherein total germination of the seed is increased by at least 3-fold under drought conditions relative to a seed that is not treated with the supersaturated bentonite slurry plug.

21. The method of claim 18, wherein the rate of germination of the seed is decreased by at least 2 days under drought conditions relative to a seed that is not treated with the supersaturated bentonite slurry plug.

22. The method of claim 17, wherein the germination of the seed grown in contact with the bentonite slurry plug is enhanced under drought conditions.

23. The method of claim 17, wherein the supersaturated bentonite slurry plug further comprises at least one compound selected from the group consisting of a fertilizer, a plant growth regulator, a fungicide, an insecticide, an amino acid, a peptide, a protein, and a nucleic acid.

24. The method of claim 23, wherein the plant growth regulator is selected from the group consisting of auxins, giberellins, cytokinins, ethylene-related compounds, abscisic acid, brassinosteroids, jasmonates, polyamines, karrikins, and any combination thereof.

25. The method of claim 23, wherein the fertilizer comprises a micronutrient.

26. The method of claim 17, wherein the bentonite of the supersaturated bentonite slurry plug is selected from the group consisting of sodium bentonite and calcium bentonite.

27. The method of claim 17, wherein the supersaturated bentonite slurry comprises at least about 50% w/w of water and from about 10% to about 50% w/w of bentonite.

28. The method of claim 17, wherein the supersaturated bentonite slurry plug is at least twice the size of the seed.

29. The method of claim 17, wherein the supersaturated bentonite slurry plug comprises from about 5% to about 20% w/w of bentonite.

30. The method of claim 17, wherein the plant growth medium is soil.

* * * * *